United States Patent [19]

Umemura et al.

[11] Patent Number: 5,060,652
[45] Date of Patent: Oct. 29, 1991

[54] ULTRASONIC DIAGNOSIS APPARATUS

[75] Inventors: Shinichiro Umemura; Hiroshi Ikeda, both of Hachioji; Kageyoshi Katakura, Tokyo, all of Japan

[73] Assignee: Hitachi Medical Corp., Tokyo, Japan

[21] Appl. No.: 415,668

[22] Filed: Oct. 2, 1989

[30] Foreign Application Priority Data

Oct. 5, 1988 [JP] Japan .................................. 63-249886

[51] Int. Cl.$^5$ .............................................. A61B 8/00
[52] U.S. Cl. ................................. 128/661.01; 73/676
[58] Field of Search .................... 128/660.01, 660.02, 128/660.07; 73/597, 599, 602, 625-626

[56] References Cited

U.S. PATENT DOCUMENTS

| 4,669,311 | 6/1987 | McKinnon | 73/602 X |
| 4,759,372 | 7/1988 | Umemura et al. | 128/660.1 |
| 4,777,958 | 10/1988 | Ophir | 128/660.1 |
| 4,817,614 | 4/1989 | Hassler et al. | 73/625 X |
| 4,878,500 | 11/1989 | Ophir et al. | 128/660.01 |

Primary Examiner—Francis Jaworski
Attorney, Agent, or Firm—Antonelli, Terry Stout & Kraus

[57]     ABSTRACT

An ultrasonic diagnosis apparatus for obtaining an ultrasonic echo image upon transmission/reception of a focussed ultrasonic beam by using an ultrasonic probe having curved array transducer elements disposed in a convexity. As the delay distribution data to be used for focussing respective transducer elements, a plurality of sets of delay distribution data, each set corresponding to a particular thickness of a fat layer under a skin of a specimen, are stored in a memory. In imaging the specimen, a set of the plurality of sets of delay distribution data is selected and read in accordance with the thickness of the fat layer of the specimen to control the delay distribution of a transmission or reception signal for respective transducer elements to thereby eliminate focussing errors to be caused by the concave lens effect of the fat layer.

8 Claims, 5 Drawing Sheets

DISTANCE FROM THE CENTER OF APERTURE

ULTRASONIC DIAGNOSIS APPARATUS

BACKGROUND OF THE INVENTION

1. Field of the Invention

The present invention relates to an ultrasonic diagnosis apparatus suitable for diagnostical imaging and quantitative analysis for medical purpose.

2. Description of Related Background Art

Electronic focussing type ultrasonic diagnosis apparatus are widely used for diagnosing various parts of human body such as an abdomen, because it has an adequate imaging range covering from a near field to a far field. An example of ultrasonic diagnosis apparatus is shown in U.S. Pat. No. 4,759,372 and others. In a paper by the inventors of this invention appearing in Japanese Journal of Medical Ultrasonics, vol. 14, Supplement I, 1987, at pp. 317 to 318, discussed for a curved array transducer probe combined with impedance matching layers and an acoustic lens for narrowing a beam width in the direction perpendicular to the beam scanning direction, is beam refraction at the interlayers in the beam scanning direction influencing the focussing.

There is also described in U.S. Pat. No. 4,566,459 that an electronic focussing error occurs in a linear array transducer probe depending upon a sound speed of organ tissue to be diagnosed, and the technique of measuring an average sound speed within organs by positively using such phenomenon.

SUMMARY OF THE INVENTION

The present inv has paid attention to a sound speed difference between a fat layer under a skin in vivo and the tissue under the fat layer, particularly to a focal point shift in electronic focussing caused by individual differences of the thickness of a fat layer under a skin.

In imaging a tomogram through electronic focussing by using a linear array transducer probe, the interface between a fat layer under a skin and its underlying layer, i.e., the back surface of the fat layer under the skin, can be regarded as a plane parallel to a probe surface. The influence, upon the electronic focussing, of refraction at the back surface of the fat layer under a skin, is therefore small in the normal range of convergence angle so that a conventional ultrasonic echography has neglected this influence.

In imaging with a curved array transducer probe, however, the surface of a body has a curvature which is the same as that of the probe surface when it is pressed against the body surface, whereas the curvature of the back surface of the fat layer under the skin is smaller than the first-mentioned curvature. Because of a curvature difference between the front and back surfaces of the fat layer caused by pressing a probe on the body, and because of a sound speed difference between the fat layer and the underlying layer, the fat layer functions as a concave lens. The curvature difference becomes larger, the smaller the curvature radius of the transducer array is and the thicker the fat layer under a skin is. For this reason, if a curved array transducer probe having a relatively small curvature radius is used in an ultrasonic imaging apparatus, there arises a problem that a desired electronic focussing is not possible because of a large error caused by the concave lens effect of the fat layer under a skin depending upon individual differences of the fat layer thickness.

It is therefore an object of the present invention to provide an ultrasonic diagnosis apparatus which reduces the influence of the difference of focussing characteristics caused by individual differences of the thickness of a fat layer under a body skin in vivo.

According to one aspect of the characteristic arrangement of this invention, the ultrasonic diagnosis apparatus comprises: a variable delay element network for delaying a transmission or reception signal for each of a plurality of transducer elements of a curved array ultrasonic probe; a memory for storing a plurality of sets of delay amounts for respective elements of the variable delay element network, each set corresponding to a particular thickness of the fat layer under a skin of an object specimen; and a control means for reading one set among the plurality of sets of delay amounts from the memory in accordance with a selection signal or an automatically measured fat layer thickness, and controlling the delay amount of each delay element in the variable delay element The other features will be clarified in the following description of the embodiments.

DESCRIPTION OF THE PREFERRED EMBODIMENTS

A first embodiment of the ultrasonic diagnosis apparatus according to this invention will be described in detail with reference to FIGS. 1 to 3.

Figure 1:
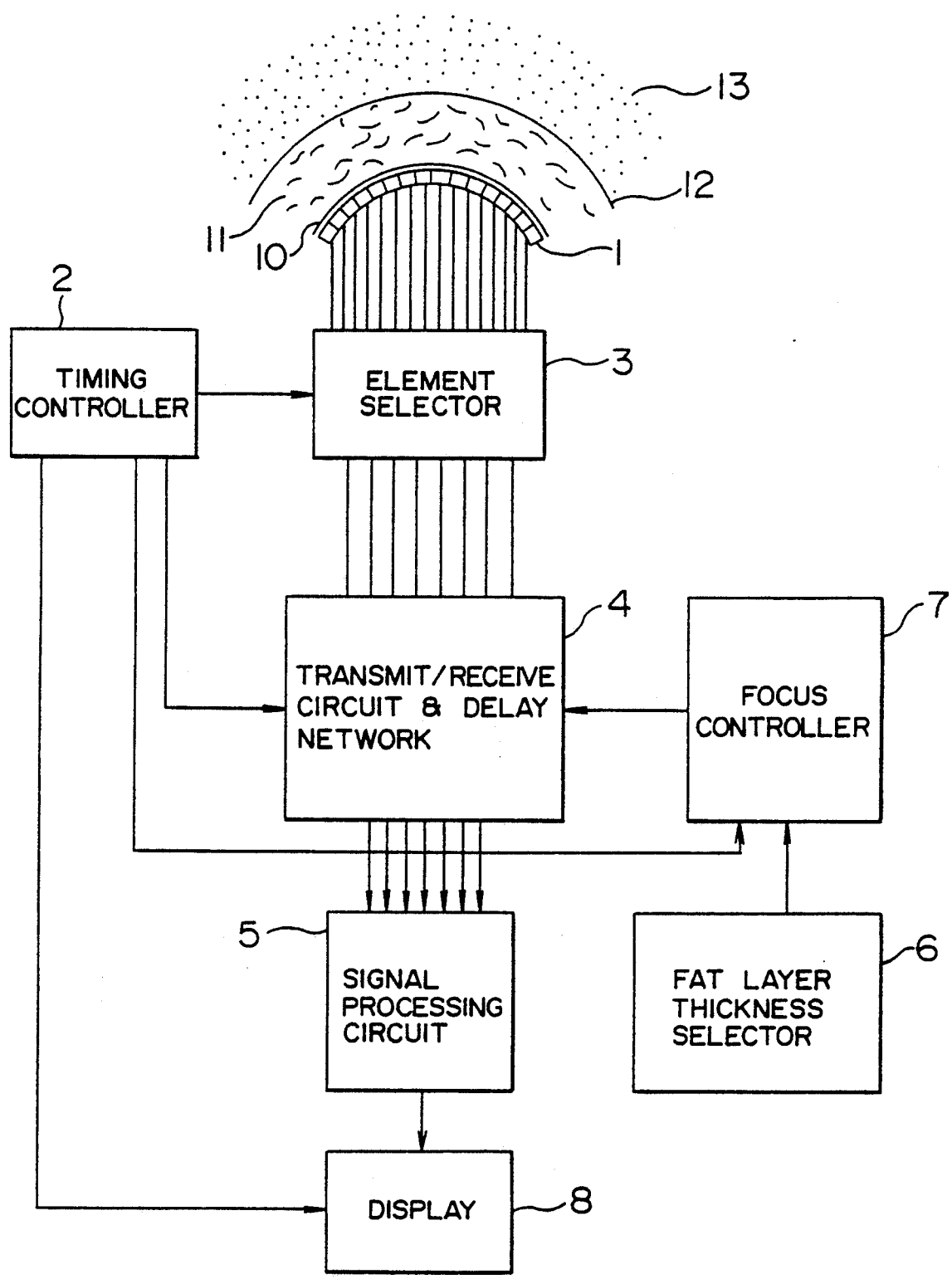
FIG. 1 is a block diagram showing an embodiment of the ultrasonic diagnosis apparatus according to the present invention.

Referring to FIG. 1, when an ultrasonic probe having convexly disposed transducer elements is softly pressed against a body to be diagnosed, a fat layer 11 under a skin is curved along the surface of the probe. Under control of a timing controller 2, an element selector 3 selects a group of signal lines led from adjoining transducer elements among all the transducer elements constituting the transducer array, the selected group defining the transmission/reception aperture.

Repeatedly supplied from a transmit/receive circuit and delay network 4 to the selected element group are drive signals of continuous pulsed wave having a delay distribution suitable for a desired focussing. The reflected and received signals are also given a distributed delay time, and are added together to be supplied to a signal processing circuit 5. An envelope signal subjected to a compression process and high frequency emphasizing process is displayed as a tomogram on a display 8 under control of the timing controller 2.

Figure 2:
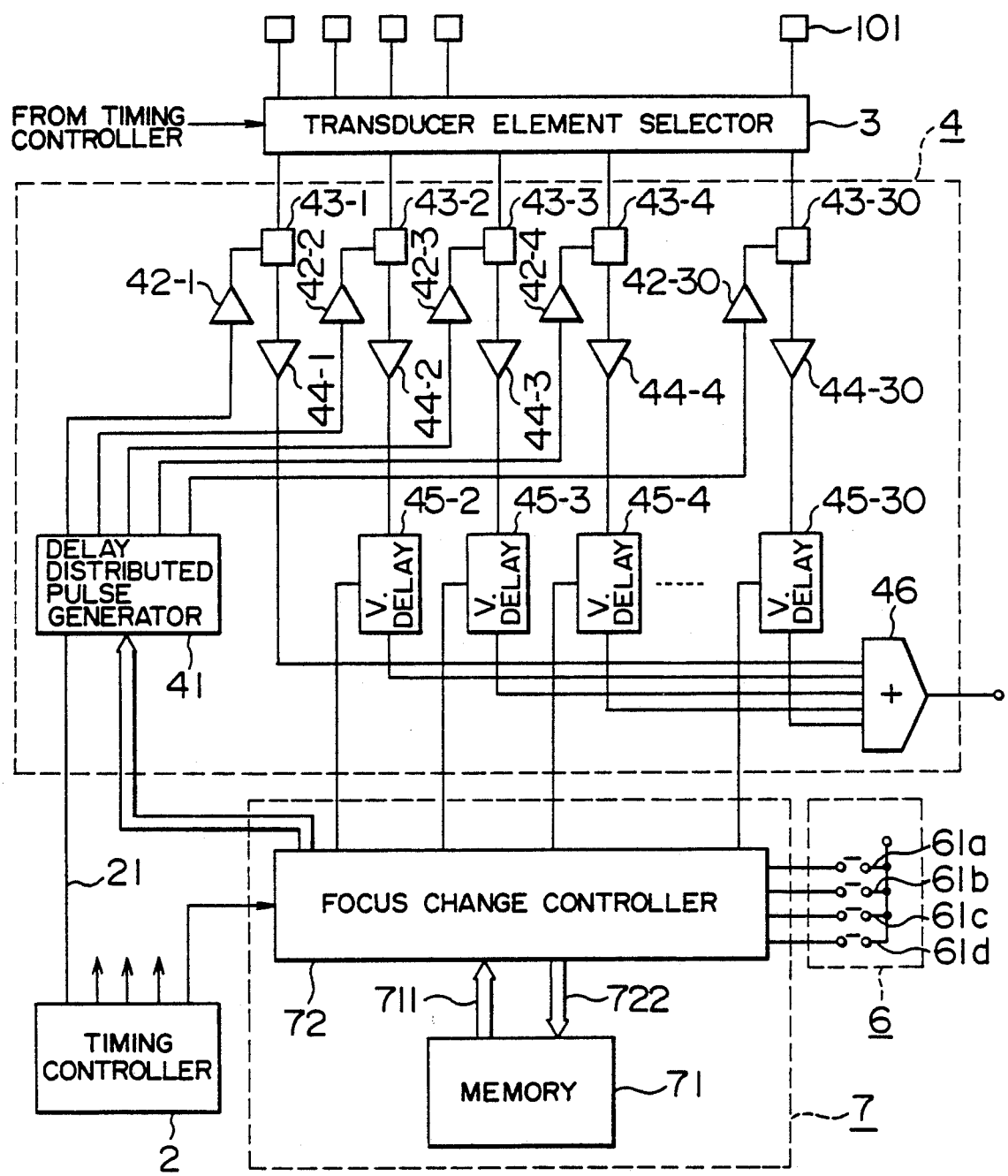
FIGS. 2 and 3 are block diagrams detailing the main part of the embodiment shown in FIG. 1.

FIG. 2 is a more detailed block diagram showing the main part of the embodiment shown in FIG. 1. Transducer elements 101, for example, one hundred and twenty four transducer elements, are disposed on the probe. Signal lines from sixty consecutive transducer elements are selected by the element selector 3. Thirty pairs of signal lines symmetrically disposed relative to the center of the selected signal lines are each connected together to form thirty channel signal lines to the transmit/receive circuit and delay network 4. The channel connected with two elements disposed side by side at the center of the selected elements is called an address 1 channel, the channel connected with next two elements disposed aside the address 1 channel elements in the outward direction is called an address 2 channel, and similarly address 3 channel, address 4 channel and so on. Every time transmission and reception are made, the selected elements are shifted by one element by the element selector 3 so that sixty four reception/transmission apertures are sequentially set one after another.

A delay distributed pulse generator 41 in the circuit 4 generates, in response to a trigger pulse 21 from the timing controller, thirty channel transmission pulses having a delay distribution for focussing a transmission beam. A transmission pulse for each channel is applied to each drive amplifier 42-1, 42-2, ..., 42-30 having a resonance circuit of a predetermined resonance frequency. Each drive amplifier generates a drive signal composed of two to three high-voltage and high-frequency pulse waves, which drive signal is then applied to each selected transducer element via a diode coupler 43-1, 43-2, ..., 43-30. An ultrasonic wave of continuous pulsed wave is therefore radiated from the probe into the body to be diagnosed.

The radiated ultrasonic wave reflected within the body is received by each transducer. The received signals at the selected 60 elements are supplied via the diode couplers 43-1, 43-2, ..., 43-30 to reception amplifiers 44-1, 44-2, ..., 44-30 which amplify the signals. An output from an address 1 channel amplifier among the thirty channel amplifiers is applied directly to an adder 46, whereas the outputs from the other addresses 2 to 30 channel amplifiers are applied via variable delay circuits 45-2, 45-3, ..., 45-30 to the adder 46. Each delay circuit has a delay line 451 having a plurality of taps as shown in FIG. 3, and switches 452 for connection between the taps and an output terminal 453. One of the switches is selected in accordance with a control signal from the focus controller 7 so that the delay amount of the delay line 451 is determined.

The focus controller 7 is constructed of a memory 71 and a focus change controller 72. The memory 71 stores delay amount data. The focus change controller 72 reads the delay amount data from the memory 71 and determines a delay distribution which defines the operation of the variable delay circuits 45-2, 45-3, ..., 45-30 and the delay distributed pulse generator 41. Specifically in this embodiment, the technique called multiple zone focussing is used whereby a tomogram of high resolution can be obtained over the broad range of depth of the body by selectively using a plurality of transmission/reception focal points. To this end, every time ultrasonic scanning completes one cycle of sequential shifts of the transmission/reception aperture, the focus change controller 72 reads the delay amount data from the memory 71 at different addresses to thereby sequentially designate three focal distances of 30 mm, 60 mm and 120 mm. Selected as the delay amount data for focussing at each focal distance is one of four sets of delay amount data each set corresponding to a particular thickness of the fat layer under a skin of the body to be diagnosed. The fat layer selector 6 has four designation switches 61a, 61b, 61c and 61d. Prior to imaging, an operator selects one of the switches in accordance with the thickness of the fat layer under a skin of the body to be diagnosed. The focus change controller 72 sequentially generates address signals 722 for reading the memory 71 in order to sequentially designate the three different focal distances. Two bits of the address signal are determined by an output from the selected switch.

Figure 3:
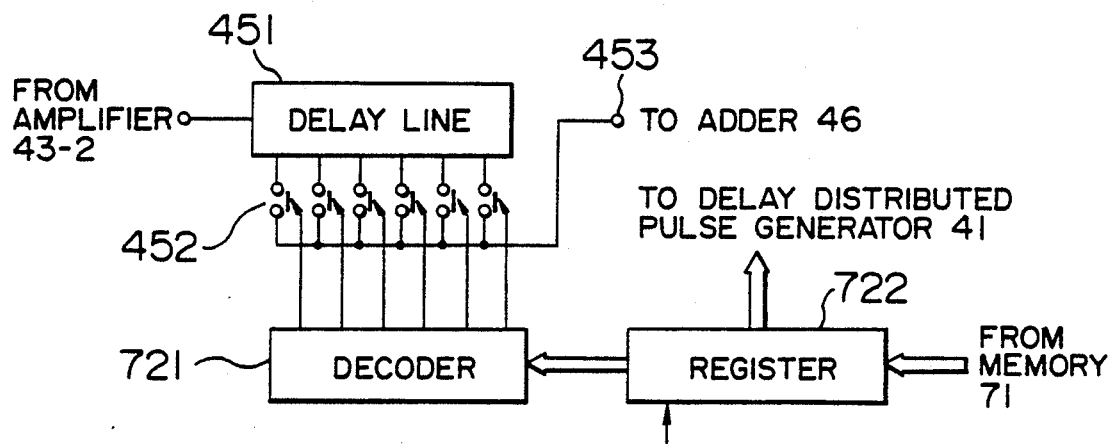

FIG. 3 shows the circuit portion of the focus change controller 72 where a control signal is generated. The delay data read from the memory 71, e.g., delay data for the element address 2, are loaded in a register 723. A decoder 721 decodes the delay data from the register 723 into a control signal by which one of the switches 452 is selected and turned on. Similar decoders and registers are provided for the other element addresses. The delay data in each register are supplied to the delay distributed pulse generator 41 for designation of a delay distribution.

Table 1 shows the delay data stored in the memory 72.

TABLE 1

| element address | data set | | | | | | | | | | | |
|---|---|---|---|---|---|---|---|---|---|---|---|---|
| | $A_1$ | $B_1$ | $C_1$ | $A_2$ | $B_2$ | $C_2$ | $A_3$ | $B_3$ | $C_3$ | $A_4$ | $B_4$ | $C_4$ |
| | d = 1 mm | | | 5 mm | | | 10 mm | | | 20 mm | | |
| | focal distance (mm) | | | focal distance (mm) | | | focal distance (mm) | | | focal distance (mm) | | |
| | 30 | 60 | 120 | 30 | 60 | 120 | 30 | 60 | 120 | 30 | 60 | 120 |
| 1 | 0 | 0 | 0 | 0 | 0 | 0 | 0 | 0 | 0 | 0 | 0 | 0 |
| 2 | 9 | 8 | 8 | 9 | 8 | 8 | 10 | 9 | 8 | 10 | 9 | 8 |
| 3 | 18 | 16 | 15 | 18 | 17 | 16 | 19 | 17 | 16 | 19 | 17 | 16 |
| 4 | 26 | 24 | 22 | 27 | 24 | 23 | 28 | 25 | 23 | 28 | 25 | 24 |
| 5 | 35 | 31 | 29 | 36 | 32 | 30 | 36 | 33 | 31 | 37 | 33 | 31 |
| 6 | 43 | 38 | 36 | 44 | 40 | 37 | 45 | 40 | 38 | 46 | 41 | 38 |
| 7 | 50 | 45 | 43 | 52 | 47 | 44 | 53 | 48 | 45 | 54 | 48 | 45 |
| 8 | 58 | 52 | 49 | 60 | 54 | 50 | 61 | 55 | 51 | 62 | 55 | 52 |
| 9 | 65 | 58 | 55 | 67 | 60 | 56 | 69 | 61 | 57 | 70 | 62 | 58 |
| 10 | 72 | 65 | 61 | 74 | 66 | 62 | 76 | 68 | 63 | 77 | 69 | 64 |
| 11 | 78 | 70 | 66 | 81 | 73 | 68 | 83 | 74 | 69 | 84 | 75 | 70 |
| 12 | 85 | 76 | 71 | 88 | 78 | 73 | 89 | 80 | 75 | 91 | 81 | 76 |
| 13 | 91 | 81 | 76 | 94 | 84 | 78 | 96 | 85 | 80 | 98 | 87 | 81 |
| 14 | 96 | 86 | 81 | 100 | 89 | 83 | 102 | 91 | 85 | 104 | 92 | 86 |
| 15 | 102 | 91 | 85 | 105 | 94 | 88 | 107 | 96 | 89 | 109 | 97 | 91 |
| 16 | 107 | 96 | 90 | 111 | 98 | 92 | 113 | 100 | 94 | 115 | 102 | 95 |
| 17 | 112 | 100 | 94 | 115 | 103 | 96 | 118 | 105 | 98 | 120 | 106 | 99 |
| 18 | 116 | 104 | 97 | 120 | 107 | 100 | 122 | 109 | 102 | 125 | 111 | 103 |
| 19 | 120 | 107 | 101 | 124 | 111 | 103 | 127 | 113 | 105 | 129 | 115 | 107 |
| 20 | 124 | 111 | 104 | 128 | 114 | 106 | 131 | 116 | 108 | 133 | 118 | 110 |

TABLE 1-continued

| element address | data set | | | | | | | | | | | |
|---|---|---|---|---|---|---|---|---|---|---|---|---|
| | $A_1$ | $B_1$ | $C_1$ | $A_2$ | $B_2$ | $C_2$ | $A_3$ | $B_3$ | $C_3$ | $A_4$ | $B_4$ | $C_4$ |
| | d = 1 mm | | | 5 mm | | | 10 mm | | | 20 mm | | |
| | focal distance (mm) | | | focal distance (mm) | | | focal distance (mm) | | | focal distance (mm) | | |
| | 30 | 60 | 120 | 30 | 60 | 120 | 30 | 60 | 120 | 30 | 60 | 120 |
| 21 | 127 | 114 | 106 | 132 | 117 | 109 | 134 | 119 | 111 | 137 | 121 | 113 |
| 22 | 131 | 116 | 109 | 135 | 120 | 112 | 138 | 122 | 114 | 140 | 124 | 116 |
| 23 | 133 | 119 | 111 | 138 | 122 | 114 | 141 | 125 | 117 | 143 | 127 | 118 |
| 24 | 136 | 121 | 113 | 140 | 125 | 116 | 143 | 127 | 118 | 146 | 129 | 120 |
| 25 | 138 | 123 | 115 | 142 | 126 | 118 | 145 | 129 | 120 | 148 | 131 | 122 |
| 26 | 140 | 124 | 116 | 144 | 128 | 120 | 147 | 130 | 122 | 150 | 133 | 124 |
| 27 | 141 | 126 | 118 | 146 | 129 | 121 | 149 | 132 | 123 | 152 | 134 | 125 |
| 28 | 142 | 127 | 118 | 147 | 130 | 122 | 150 | 133 | 124 | 153 | 135 | 126 |
| 29 | 143 | 127 | 119 | 147 | 131 | 122 | 151 | 133 | 124 | 153 | 136 | 126 |
| 30 | 143 | 127 | 119 | 148 | 131 | 122 | 151 | 134 | 125 | 154 | 136 | 127 |

The data set at column A1 shows a delay amount distribution for the fat layer thickness of 1 mm and focal distance of 30 mm. Values entered in each line indicate the delay amount (10 nsec unit) of each element at address 1 to 30. Similarly, the data set at column B1 is for the fat layer thickness of 1 mm and focal distance of 60 mm, and the data set at column C1 for the fat layer thickness of 1 mm and focal distance of 120 mm. The columns A2, B2 and C2 indicate the delay amount distribution for the fat layer thickness of 5 mm, the columns A3, B3 and C3 for the fat layer thickness of 10 mm, and the columns A4, B4 and C4 for the fat layer thickness of 20 mm, respectively for each focal distance. From the delay amount data stored in a two-dimensional memory map, the data set for a particular column is read to set the delay amount distribution. The particular column is located at the read addresses identified by the fat layer thickness and focal distance.

The delay data shown in Table 1 were calculated while taking into consideration of the concave lens effect by the fat layer under a skin, where the transducer element pitch is 0.2 mm, the element array curvature radius is 10 mm, the sound speed in a fat layer is 1430 m/s, and the average sound speed within a body except the fat layer is 1530 m/s. Such delay data are calculated accurately by numerical computation, but can be approximately calculated in the following manner.

Taking the focal distance as $f_0$ which is determined on the basis of an average acoustic velocity of a specimen body except the fat layer while assuming that the fat layer is not present, the focal distance $f_1$ of a focussed ultrasonic wave incident from the transducer array into the fat layer is represented as in the following, in accordance with the fundamental equation describing the reflection at a spherical or cylindrical surface.

$$1/f_1 = a/f_0 - (1-a)/R \quad (1)$$

When the probe is pressed against the body, the fat layer is curved as shown in FIG. 1. Assuming that the fat layer thickness d is constant, the focal distance $f_2$ of a focussed ultrasonic wave incident from the body surface into the fat layer and further within the body structure is given as in the following, by using the same fundamental equation and the focal distance $f_1$.

$$a/(f_2-d) = 1/(f_1-d) + (1-a)/(R+d) \quad (2)$$

By solving the equations (1) and (2), the focal distance $f_0$ is obtained as a function of the focal distance $f_2$ to be realized, i.e., the focal distance from the transducer array to the target area. The delay distribution for respective transducer elements is stored in the memory 72 for realizing a focussing to the focal distance $f_0$ in the uniform field with the average acoustic velocity described above. Namely, the focal distance $f_0$ is obtained from $$a/f_0 = 1/f_1 + (1-a)/R,$$

where $$1/(f_1-d) = a/(f_2-d) - (1-a)/(R+d) \quad (3)$$

Figure 4:
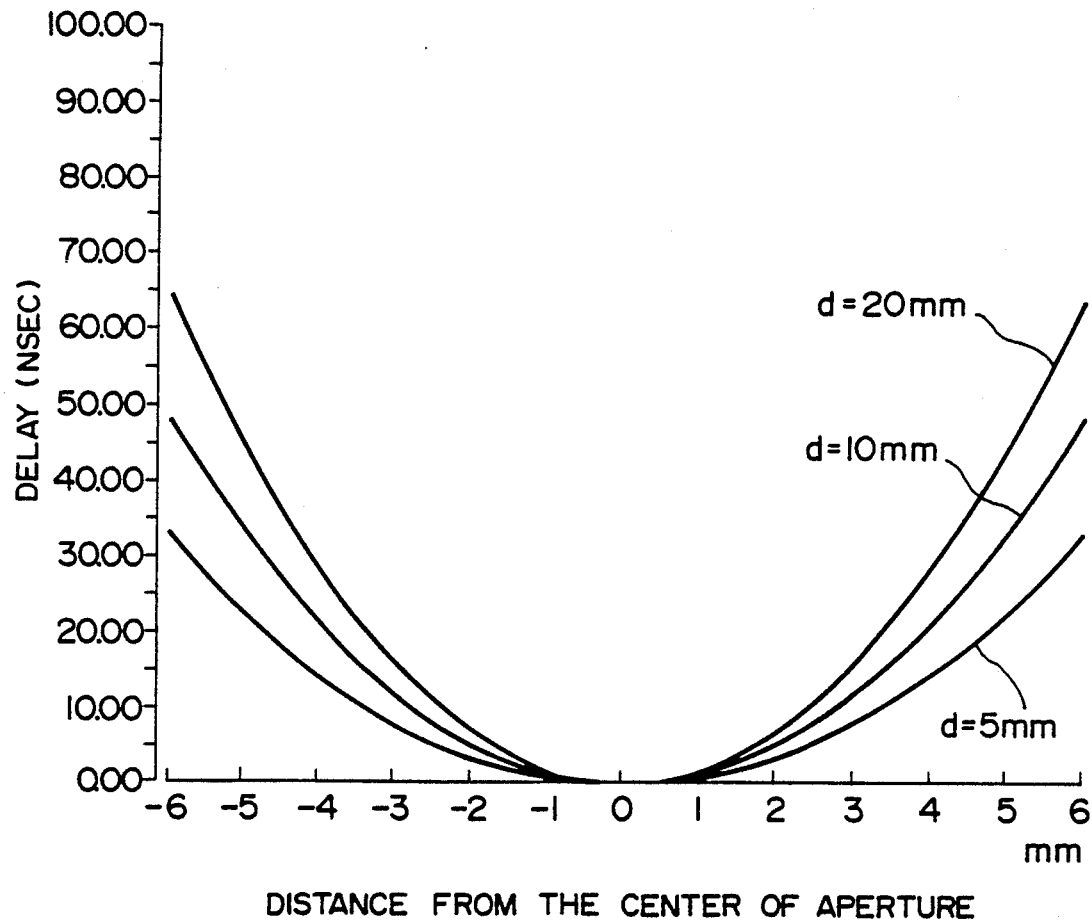
FIG. 4 is a graph showing the characteristic of delay data used in the embodiment.

The delay data calculated on the basis of the obtained focal distance $f_0$ are the values representative of the delay data determined by neglecting the presence of a fat layer added with the delay data for cancelling the fat layer concave lens effect. FIG. 4 is a graph showing the distribution of the added delay data for the focal distance 120 mm. The ordinate axis represents a difference between the delay data determined by neglecting the presence of a fat layer and the delay data determined by taking the fat layer into consideration. The abscissa axis represents a distance from an element to which delay data is supplied, to the center of the transmission/reception aperture. The concave lens effect of a fat layer generates in accordance with a difference between the curvature radius of the probe surface and that of the back surface of a fat layer. Accordingly, if the curvature radius of the probe surface, i.e., the curved array, is large, the concave lens effect can be substantially neglected. A plurality set of delay data to be selected for a particular fat layer thickness become necessary for the curvature radius of the curved array smaller than or equal to 30 mm, and in such a case, the delay data in this embodiment can advantageously be used.

In the embodiment described above, multiple zone focussing of three steps is carried out. An image to be obtained is classified into three zones with respect to the distance from the probe. An image at the first zone near the probe is obtained at the focal distance 30 mm, an image at the second zone at the intermediate distance is obtained at the focal distance 60 mm, and an image at the third zone at the far distance is obtained at the focal distance 120 mm. If multiple zone focussing is applied to the apparatus which cannot perform the selection operation of, as in this embodiment, the delay distribution data for a particular fat layer thickness, then there occurs the case that an actual focal point becomes out of the intended focal zone. In such a case, the resolution of a tomogram deteriorates considerably. In contrast, according to this embodiment, by selecting the delay data suitable for a particular fat layer thickness, it is always possible to obtain a focal point as designed and hence a tomogram of high resolution. It is particularly advantageous in that large individual differences of the thickness of a fat layer under a skin of a human body can be dealt with. This embodiment is also advantageous in imaging a tomogram while using a water bag between a probe and a specimen to enhance the acoustic coupling therebetween. The sound speed of liquid contained in a water bag is made equal to the average sound speed of a human body. However, it often happens that both the sound speeds become different because of a temperature change. If a probe is used whose curved array has a small curvature radius, the water bag takes a typical concavity shape to thereby present the concave effect similar to the fat layer. In this case, one of the switches 61a to 61d of this embodiment is selected in accordance with whether a water bag is used or not and in accordance with the sound speed of liquid within the bag, thereby cancelling the convex lens effect and allowing high resolution imaging. In this case, it can be said that a plurality of sets of delay distribution data stored in the memory 71 are the delay distribution data added with the delay amount which cancels the concave lens effect of the acoustic coupling member interposed between a probe and a specimen body.

Figure 5:
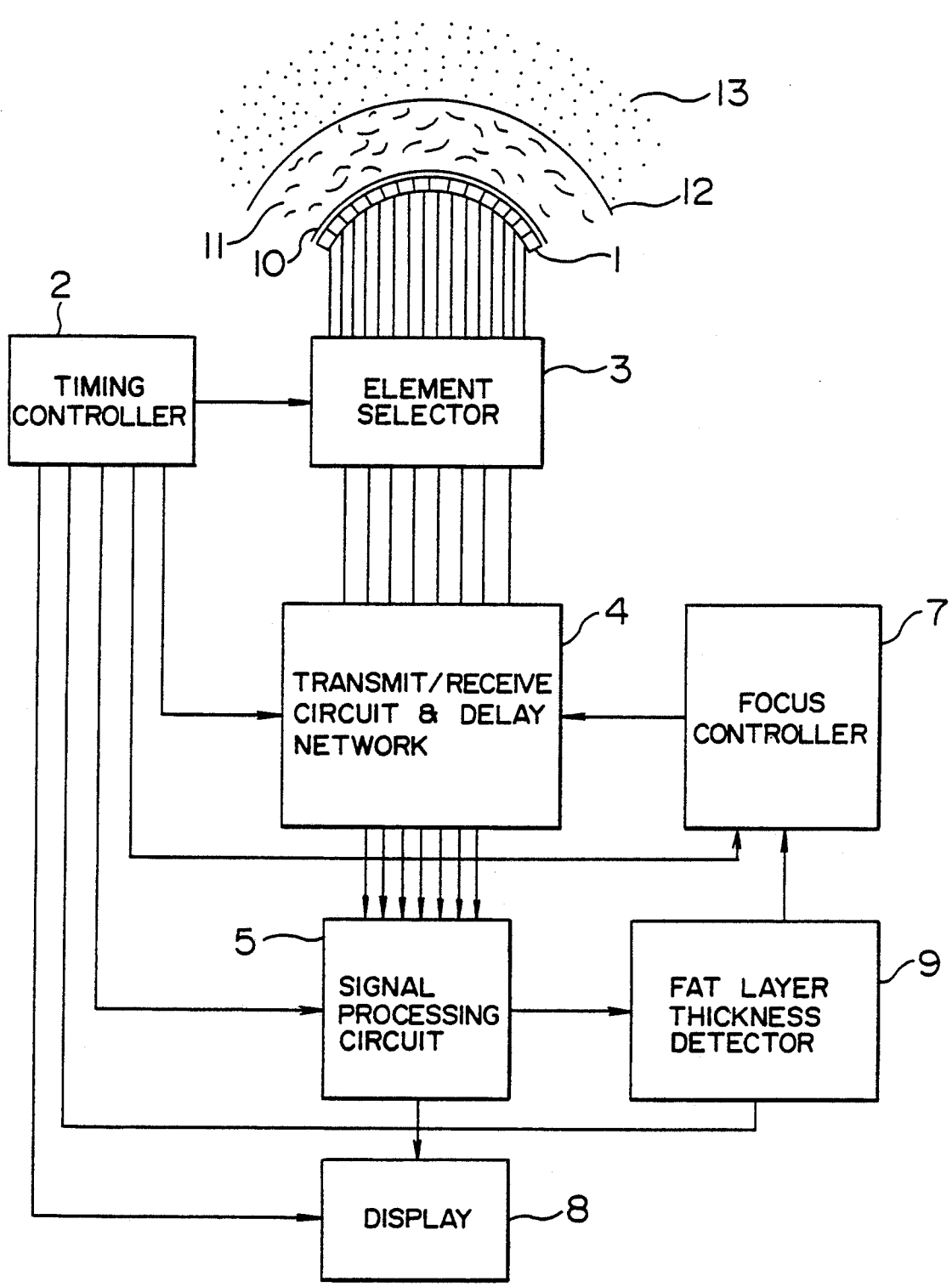
FIG. 5 is a block diagram showing another embodiment of the ultrasonic diagnosis apparatus according to the present invention.
Figure 6:
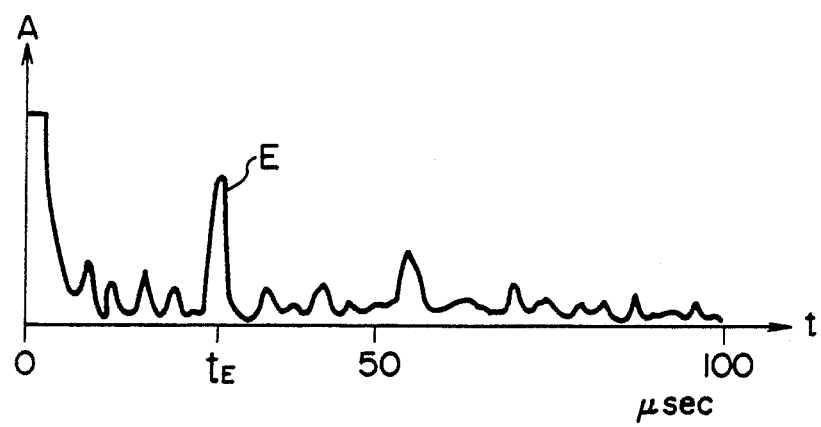
FIG. 6 shows a waveform of echo envelope in time domain used for explaining the thickness determining method in the embodiment shown in FIG. 5.
Figure 7:
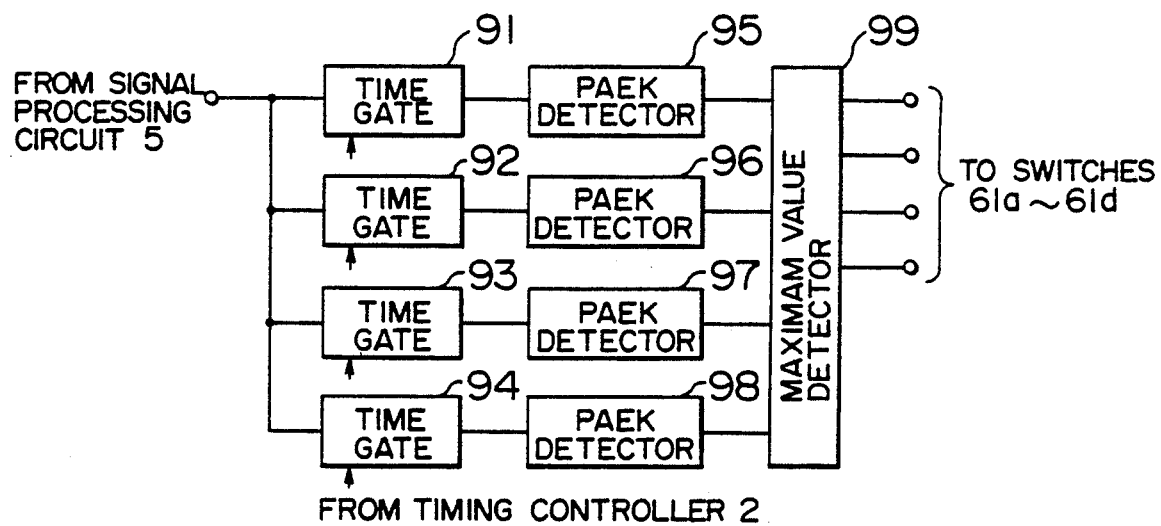
FIG. 7 is a block diagram detailing the main part of the embodiment shown in FIG. 5.

FIG. 5 shows the arrangement of another embodiment of this invention. The difference from the embodiment shown in FIG. 1 is that a fat layer thickness detector 9 is added. The fat layer thickness detector has designation switches similar to the switches 61a, 61b, 61c and 61d shown in FIG. 2. In the ordinary or basic mode, a designation switch 61a corresponding to a fat layer thickness of 1 mm is automatically selected. Upon this automatic selection, similar to the operation as described with FIGS. 1 and 2, imaging by reading the delay data starts, and the addition signal of reception signals given the delay distribution is supplied to the signal processing circuit 5. The envelope signal of the addition signal is shown in FIG. 6 by way of example. An ultrasonic echo E reflected from the back surface of the fat layer generally has a higher intensity than other echoes reflected from the shallow regions within the body. The fat layer thickness detector 9 divides the envelope signal into four stage time windows by means of four time gates 91 to 94 shown in FIG. 7, and the peak values within the respective time windows are detected by peak detectors 95, 96, 97 and 98. A maximum value detector 99 compares the outputs from the peak detectors 95 to 98 after compensating the ultrasound attenuation in propagation and detects the maximum value. A detection signal indicating that an echo E from the back surface of the fat layer is within the time window which gave the maximum value, is used for selecting one of the switches 61a to 61b. In the above manner, the apparatus shown in FIGS. 4 to 6 automatically determines the thickness of a fat layer under a skin of a specimen body so that the delay data can be selected in accordance with the determined thickness. The echo shown in FIG. 6 takes a sharper peak, the smaller the transmission/reception aperture width is set, the higher the center frequency of an ultrasonic wave is set, or the lesser the number of transmission pulsed waves is set, i.e., the broader the transmission frequency bandwidth is set. A sharper peak improves the precision in determining the time window. It is therefore effective that one or both of the transmission and reception aperture width used, for example, for an initial transmission/reception for determining the fat layer thickness, be made smaller than those aperture diameters used for imaging after the thickness determination. It is also effective that the bandwidth of the drive amplifiers is made broad only when determining the fat layer thickness.

Calculating the delay data by using the equation (3) is made on the assumption that when a probe is pressed against the body, the thickness d of the fat layer does not change, i.e., the back surface 11 of the fat layer and the front surface of the probe 1 are concentrical as shown in FIG. 1. In practice however, the fat layer near the center of the probe is depressed and becomes thinner than the other portion so that the difference between the curvature radii of the probe surface and the back surface of the fat layer become larger than that under the above-described assumption. This tendency is more remarkable, the smaller the curvature radius of the probe surface is and the thicker the original fat layer is. The fat layer concave lens effect therefore becomes larger than that under the above-described assumption. In view of this, in calculating the delay data to be stored in the memory, it is desirable to consider also the change of the thickness distribution of a fat layer caused upon depression by a probe. Further, in the embodiment shown in FIGS. 4 to 6, it is desirable to determine the fat layer thickness by measuring the fat layer distribution by using transmission/reception waves propagating in a plurality of directions upon suitable selection of transducer elements, thereby allowing a more accurate selection of delay data.

In the above embodiments, a multiple zone focussing method has been used and the focal distance same for both transmission and reception waves has been switched among three steps. The present invention is also effective for the case where the focal distance only for the reception wave is switched. Particularly in the real time dynamic focussing method whereby the focal distance of the reception wave is switched during the reception period after each transmission of the transmission wave, the focal distance is generally switched among multiple steps. In such a case, the delay distribution data corresponding to a particular fat layer thickness for each focal distance are selected to thereby obtain a high resolution image over the entire depth. In the reception wave dynamic focussing method, the focal distance is switched as the time lapses after transmission of an ultrasonic wave. In this case therefore, instead of preparing a plurality of sets of delay distribution data for each focal distance in the memory, one set of delay distribution data for each focal distance may be prepared and the focal distance switching timing may be changed in accordance with the fat layer thickness, while retaining the similar expected advantageous effect.

We claim:

1. An ultrasonic diagnosis apparatus for examining a specimen comprising:
   an ultrasonic probe having a curved array of transducer elements disposed in a convexity and having a convex surface for contacting the specimen;
   transmission/reception means for supplying a drive signal to at least a fraction of said transducer elements and for receiving a reception signal from at least a fraction of said transducer elements;
   a variable delay network having delay elements for delaying said drive signal or said reception signal for each of said transducer elements;

memory means for storing a plurality of sets of delay distribution data to be used by said variable delay network, each set including delay distribution data for forming a focal point of an ultrasonic beam for transmission or reception so that a concave lens effect on the ultrasonic beam of a fat layer under a skin of the specimen deformed by the ultrasonic probe is compensated on the assumption that the fat layer has a thickness of each of a plurality of predetermined values;

control means for selecting a set from said plurality of sets of delay distribution data in accordance with a selection input, for reading the selected set of delay distribution data from said memory means, and for controlling the delay of each delay element of said variable delay network in accordance with the read data; and image forming mean for forming and visualizing an echo image of said specimen in accordance with the reception signal obtained through said variable delay network.

2. An ultrasonic diagnosis apparatus according to claim 1, further comprising fat layer thickness determining means for generating said selection signal in accordance with a detection signal obtained by detecting the time from when a sound wave is transmitted at said transmission/reception means to when an echo of said sound wave reflected at the back surface of the fat layer under a skin of a specimen is received at said transmission/reception means.

3. An ultrasonic diagnosis apparatus according to claim 2, at least one of the transmission aperture and reception aperture of said ultrasonic probe used in transmission/reception of a sound wave for the determination by said determining means, is smaller than the transmission aperture and reception aperture of said ultrasonic probe used in forming an echo image.

4. An ultrasonic diagnosis apparatus according to claim 2, wherein the frequency bandwidth of a transmitted sound wave used for the determination by said determining means is broader than the frequency bandwidth of a transmitted sound wave used for forming an echo image.

5. An ultrasonic diagnosis apparatus according to claim 1, wherein said ultrasonic probe has a configuration of cylindrical surface along which said curved array transducer elements are disposed, and said plurality of sets of distributed delay data stored in said memory means are the delay distribution data calculated on the assumption that when said ultrasonic probe is pressed against a specimen, the back surface of the fat layer under the skin of the specimen becomes a cylindrical surface which is concentric to the surface of said ultrasonic probe.

6. An ultrasonic diagnosis apparatus according to claim 1, wherein said ultrasonic probe has a configuration of a cylindrical surface along which said curved array transducer elements are disposed, and said plurality of sets of distributed delay data stored in said memory means are the delay distribution data calculated on the assumption that when said ultrasonic probe is pressed against a specimen, the distribution of thickness of the fat layer under the skin of the specimen changes.

7. An ultrasonic diagnosis apparatus according to claim 1, wherein said memory means stores a plurality of sets of distributed delay data, each set corresponding to a particular thickness of a fat layer under a skin for each of a plurality of focal distances, and said control means sequentially changes the focal distances and selects a set of said plurality of sets of delay distribution data for each focal distance.

8. An ultrasonic diagnosis apparatus for examining a specimen comprising:

an ultrasonic probe having a curved array of transducer elements disposed in a convexity and having a convex surface for contacting the specimen;

transmission/reception means for supplying a drive signal to at least a fraction of said transducer elements and for receiving a reception signal from at least a fraction of said transducer elements;

a variable delay network having delay elements for delaying said drive signal or reception signal for each of said transducer elements;

memory means for storing a plurality of sets of delay distribution data to be used by said variable delay network, each set including delay distribution data for forming a focal point of an ultrasonic beam for transmission or reception so that a concave lens effect on the ultrasonic beam of an acoustic coupling member deformed by the ultrasonic probe and arranged between said ultrasonic probe and the specimen or to the sound speed of said acoustic coupling member is compensated;

control means for selecting a set from said plurality of sets of delay distribution data in accordance with a selection input, for reading the selected set of delay distribution data from said memory means, and for controlling the delay amount of each delay element of said variable delay network in accordance with the read data; and image forming mean for forming and visualizing an echo image of said specimen in accordance with the reception signal obtained through said variable delay network.

* * * * *